United States Patent
Mamedov et al.

(10) Patent No.: US 9,688,593 B2
(45) Date of Patent: Jun. 27, 2017

(54) METHOD FOR CARBON DIOXIDE HYDROGENATION OF SYNGAS AND THE INTEGRATION OF THE PROCESS WITH SYNGAS CONVERSION PROCESSES

(71) Applicant: SAUDI BASIC INDUSTRIES CORPORATION, Riyadh (SA)

(72) Inventors: Aghaddin Mamedov, Houston, TX (US); Clark Rea, Houston, TX (US)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 15/033,255

(22) PCT Filed: Oct. 29, 2014

(86) PCT No.: PCT/US2014/062789
§ 371 (c)(1),
(2) Date: Apr. 29, 2016

(87) PCT Pub. No.: WO2015/066117
PCT Pub. Date: May 7, 2015

(65) Prior Publication Data
US 2016/0280618 A1    Sep. 29, 2016

Related U.S. Application Data (60) Provisional application No. 61/896,943, filed on Oct. 29, 2013.

(51) Int. Cl.
*C07C 29/151* (2006.01)
*C01B 3/38* (2006.01)
(Continued)

(52) U.S. Cl.
CPC ........... *C07C 29/1518* (2013.01); *B01J 23/26* (2013.01); *B01J 23/34* (2013.01); *B01J 23/883* (2013.01);
(Continued)

(58) Field of Classification Search
CPC . C01B 3/16; C01B 31/18; C01B 31/16; B01J 2523/847; C07C 31/04; C07C 29/151; C07C 29/1518
(Continued)

(56) References Cited

U.S. PATENT DOCUMENTS 1,913,364 A    6/1933    Bader
5,346,679 A    9/1994    Osaki et al.
(Continued)

FOREIGN PATENT DOCUMENTS

EP    1445232 A1    8/2004
GB    2168718 A    6/1986
(Continued)

OTHER PUBLICATIONS

International Search Report for International Application No. PCT/US2014/062789; International Filing Date: Oct. 29, 2014; Date of Mailing: Feb. 25, 2015; 4 Pages.
(Continued)

*Primary Examiner* — Jafar Parsa
(74) *Attorney, Agent, or Firm* — Cantor Colburn LLP (57) ABSTRACT

Techniques for synthesizing methanol are provided. In an exemplary embodiment, the processes include obtaining a syngas mixture from an integrated carbon dioxide hydrogenation process and a methane steam reforming process, and contacting the syngas mixture with a methanol catalyst to obtain a product stream comprising methanol.

20 Claims, 2 Drawing Sheets

(51) Int. Cl.
  *B01J 23/883* (2006.01)
  *B01J 23/34* (2006.01)
  *B01J 23/26* (2006.01)

(52) U.S. Cl.
  CPC ............... *C01B 3/38* (2013.01); *C01B 3/382* (2013.01); *C01B 3/386* (2013.01); *C01B 2203/0233* (2013.01); *C01B 2203/0495* (2013.01); *C01B 2203/061* (2013.01); *C01B 2203/0833* (2013.01); *C01B 2203/1058* (2013.01); *C01B 2203/1241* (2013.01); *Y02P 20/142* (2015.11); *Y02P 20/52* (2015.11); *Y02P 20/582* (2015.11)

(58) Field of Classification Search
  USPC ................................................ 518/700, 702
  See application file for complete search history.

(56) References Cited

U.S. PATENT DOCUMENTS

| | | | |
|---|---|---|---|
| 5,496,530 A | | 3/1996 | Vannby et al. |
| 6,312,658 B1 | * | 11/2001 | Hufton .................. B01D 53/02 423/418.2 |
| 8,288,446 B2 | | 10/2012 | Mamedov et al. |
| 2003/0113244 A1 | | 6/2003 | Dupont et al. |
| 2005/0026093 A1 | | 2/2005 | Ohzeki |
| 2010/0150466 A1 | | 6/2010 | Koh |
| 2010/0190874 A1 | | 7/2010 | Mamedov et al. |
| 2011/0105630 A1 | | 5/2011 | Dorner et al. |
| 2012/0007025 A1 | | 1/2012 | Mamedov |
| 2013/0150466 A1 | | 6/2013 | Mamedov et al. |

FOREIGN PATENT DOCUMENTS

| | | |
|---|---|---|
| GB | 2279583 A | 1/1995 |
| WO | 9606064 A1 | 2/1996 |

OTHER PUBLICATIONS

Written Opinion of the International Searching Authority for International Application No. PCT/US2014/062789; International Filing Date: Oct. 29, 2014; Date of Mailing; Feb. 25, 2015; 4 Pages.

* cited by examiner

METHOD FOR CARBON DIOXIDE HYDROGENATION OF SYNGAS AND THE INTEGRATION OF THE PROCESS WITH SYNGAS CONVERSION PROCESSES

CROSS REFERENCE TO RELATED APPLICATIONS

This application is a 371 of International Application No. PCT/US2014/062789, filed Oct. 29, 2014, which claims priority to U.S. Application No. 61/896,943, filed Oct. 29, 2013, both of which are incorporated herein by reference in their entirety.

TECHNICAL FIELD

The presently disclosed subject matter relates to processes and apparatuses for synthesizing methanol.

BACKGROUND

Methanol is a commodity used in various areas. It can be converted to formaldehyde which is used to make synthetic polymers or to mix with other materials. Methanol can also be used to make a wide variety of chemicals including dimethyltoluene, methylamines, chlorinated solvents, acetic acid, isoprene, or used in fuels. Elevated environmental standards and limited oil supplies can yield an increasing demand in methanol in the future.

The synthesis of methanol can be achieved through a synthesis gas (syngas). Syngas contains hydrogen ($H_2$) and carbon monoxide (CO), may further contain other gas components, e.g., carbon dioxide ($CO_2$), water ($H_2O$), methane ($CH_4$), and/or nitrogen ($N_2$). Carbon oxides react with hydrogen to form methanol according to the following equations:

$$CO+2H_2=CH_3OH$$

$$CO_2+3H_2=CH_3OH+H_2O$$

The composition of syngas is characterized mainly by its $H_2$ and CO content; generally presented by the so-called stoichiometric number (SN), which is defined as:

$$SN=([H_2]-[CO_2])/([CO]+[CO_2])$$

where the concentrations of components are expressed in vol % or mol %.

In the past, processes have been developed to produce syngas. Natural gas and light hydrocarbons are the predominant starting materials for making syngas. Such syngas processes frequently use methane as a starting material, which may be converted to syngas by steam reforming, partial oxidation, $CO_2$ reforming, or by a so-called autothermal reforming reaction. One technology for producing syngas from a methane feedstock is the reaction with water (steam) at high temperatures, generally called hydrocarbon steam reforming.

If a feedstock is used in a reforming process that is rich in higher hydrocarbons, like naphtha, the feedstock first needs to be treated in a so-called pre-reforming step, in order to convert the heavy hydrocarbons in the feed into methane, hydrogen and carbon oxides. Such higher hydrocarbons are more reactive than methane in steam reforming, and would—if present in the feed—lead to carbon formation and thus to deactivation of the catalyst employed in steam reforming. In such a pre-reformer, several reactions take place simultaneously; the most important being hydrocarbon steam reforming (1), water gas shift (2), and methanation (3) reactions, which can be represented, respectively, as:

$$C_nH_m+nH_2O \leftrightarrows nCO+(m/2+n)H_2 \quad (1)$$

$$CO+H_2O \leftrightarrows CO_2+H_2 \quad (2)$$

$$CO+3H_2 \leftrightarrows CH_4+H_2O$$

$$CO_2+4H_2 \leftrightarrows CH_4+2H_2O \quad (3)$$

Such a pre-reformer is typically operated adiabatically at temperatures between about 320° C. and 550° C.

In a steam methane reformer (SMR), methane-rich gas is converted into a mixture containing carbon monoxide, carbon dioxide, hydrogen and unreacted methane and water in the so-called steam reforming (4) and carbon dioxide reforming (5) reactions, represented as:

$$CH_4+H_2O \leftrightarrows CO+3H_2 \quad (4)$$

$$CH_4+CO_2 \leftrightarrows 2CO+2H_2 \quad (5)$$

One disadvantage associated with syngas production by methane steam reforming is that the composition of the produced gas mixture is limited by the reaction stoichiometry to $H_2$/CO ratios of 3 or higher.

In order to avoid such drawbacks and to help counteract increasing $CO_2$ concentrations in the atmosphere, attempts have been made to manufacture syngas from $CO_2$ as a raw material. The conversion is based on the following equation:

$$CO+H_2O \leftrightarrows CO_2+H_2$$

The forward reaction is known as the water gas shift (WGS) reaction, while the reverse reaction is known as the reverse water gas shift (RWGS) reaction.

Conversion of $CO_2$ to CO by a catalytic RWGS reaction can be a process for $CO_2$ utilization. Early work proposed iron oxide/chromium oxide (chromite) catalysts for this endothermic reaction; see, e.g., U.S. Pat. No. 1,913,364. However, such catalysts can suffer from methane formation and the accompanying catalyst coking problem.

GB 2168718A discloses combining the RWGS reaction with steam reforming of methane. The combination of the two reactions allowed the molar ratio of $H_2$:CO to be adjusted and to better control the SN value in the final syngas mixture to values of about 3 or higher, depending on the intended subsequent use of the syngas mixture.

GB 2279583A discloses a catalyst for the reduction of $CO_2$, which comprises at least one transition metal selected from Group VIII metals and Group VIa metals supported on ZnO alone, or on a composite support material containing ZnO. In order to suppress $CH_4$ formation and catalyst deactivation, stoichiometric $H_2/CO_2$ mixtures and low reaction temperatures were used, which resulted in relatively low $CO_2$ conversion.

U.S. Pat. No. 5,346,679 discloses the reduction of $CO_2$ into CO with $H_2$ using a catalyst based on tungsten sulphide. U.S. Pat. No. 3,479,149 discloses using crystalline aluminosilicates as catalyst in the conversion of CO and water to $CO_2$ and $H_2$, and vice versa.

U.S. Pat. No. 5,496,530 discloses $CO_2$ hydrogenation to syngas in the presence of nickel and iron oxide and copper or zinc containing catalysts. In WO 96/06064A1, a process for methanol production is described, which includes a step of converting part of the $CO_2$ contained in a feed mixture with $H_2$ to CO, in the presence of a WGS catalyst exemplified by Zn—Cr/alumina and $MoO_3$/alumina catalysts.

WO 2005/026093A1 discloses a process for producing dimethylether (DME), which includes a step of reacting $CO_2$ with $H_2$ in a RWGS reactor to provide carbon monoxide, in the presence of a ZnO supported catalyst; a $MnO_x$ (=1~2) supported catalyst; an alkaline earth metal oxide supported catalyst and a NiO supported catalyst. EP 1445232A2 discloses a RWGS reaction for production of CO by hydrogenation of $CO_2$ at high temperatures, in the presence of a Mn—Zr oxide catalyst.

United States Patent Publication No. 2003/0113244A1 discloses a process for the production of a syngas mixture that is rich in CO, by converting a gas phase mixture of $CO_2$ and $H_2$ in the presence of a catalyst based on zinc oxide and chromium oxide, but not including iron. The presence of both Zn and Cr was indicated to be essential for formation of CO and $H_2$ mixture at a good reaction rate, whereas the presence of Fe and/or Ni is to be avoided to suppress formation of $CH_4$ via so-called methanation side-reactions. Formation of $CH_4$ as a by-product is generally not desired, because its production reduces CO production. The co-production of $CH_4$ may also reduce catalyst life-time by coke formation and deposition thereof. A drawback of the process for syngas production disclosed in U.S. 2003/0113244A1 is the selectivity of the catalyst employed; that is $CH_4$ formation from $CO_2$ is still observed as a side-reaction. In the illustrative example, this $CH_4$ formation was quantified as 0.8 vol % of $CH_4$ being formed in the gas output of the reactor, at a degree of conversion of $CO_2$ of 40%.

In addition, U.S. Patent Publication Nos.: 2010/0190874 and 2010/0150466 disclose processes of making syngas including CO, $CO_2$ and $H_2$ under an isothermal conditions by contacting a gaseous feed mixture including $CO_2$ and $H_2$ with a catalyst including Mn oxide and an auxiliary metals, e.g., La, W, etc.

There remains a need in the art for improved and less energy consuming processes for synthesizing methanol.

SUMMARY

A process of synthesizing methanol comprises: obtaining a syngas mixture from an integrated carbon dioxide hydrogenation process and a methane steam reforming process, wherein the carbon dioxide hydrogenation process comprises contacting a gaseous feed mixture comprising carbon dioxide and hydrogen with a carbon dioxide hydrogenation catalyst; and the methane steam reforming process comprises contacting a desulphurised gaseous hydrocarbon feedstock and steam with a methane reforming catalyst; and contacting the syngas mixture with a methanol catalyst to obtain a product stream comprising methanol.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same

DETAILED DESCRIPTION

The presently disclosed subject matter provides novel processes for synthesizing methanol.

The presently disclosed subject matter provides processes for synthesizing methanol. The processes include obtaining a syngas mixture from an integrated carbon dioxide hydrogenation process and a methane steam reforming process. The carbon dioxide hydrogenation process can include contacting a gaseous feed mixture that includes carbon dioxide and hydrogen with a carbon dioxide hydrogenation catalyst. The methane steam reforming process can include contacting a desulphurised gaseous hydrocarbon feedstock and steam with a methane reforming catalyst. The processes can further include contacting the syngas mixture with a methanol catalyst to obtain a product stream including methanol, and removing water from the syngas mixture prior to contacting the syngas mixture with the methanol catalyst.

In accordance with the presently disclosed subject matter, the desulphurised gaseous hydrocarbon feedstock can be a methane-rich feedstock including at least about 75 mol % of methane. The desulphurised gaseous hydrocarbon feedstock is mixed with the steam at a steam/carbon ratio of from about 2.0 to about 3.5. The desulphurised gaseous hydrocarbon feedstock mixed with the steam can be fed to a gas heated reformer and a steam methane reformer operated in series. In certain embodiments, the desulphurised gaseous hydrocarbon feedstock mixed with the steam can be pre-heated to from about 500° C. to about 550° C. and then fed to the gas heated reformer. In some embodiments, the reformed gas coming from the gas heated reformer has a temperature of from about 600° C. to about 700° C., and is subsequently fed to the steam methane reformer.

The syngas mixture of the presently disclosed subject matter includes carbon monoxide, carbon dioxide, and hydrogen. In certain embodiments, the syngas mixture has a stoichiometric number of about 2.0.

The methane reforming catalyst can include nickel. The carbon dioxide hydrogenation catalyst can include a Mn oxide, and an oxide of at least one member selected from the group consisting of Cr, Ni, La, Ce, W and Pt. Additionally or alternatively, the carbon dioxide hydrogenation catalyst can include Ni and a support material. The support material can be lanthana ($La_2O_3$). In another embodiment, the carbon dioxide hydrogenation catalyst can include chromium, which can further include a promoter comprising one alkali metal or alkaline earth metal, and/or a support material. The support material can be alumina. Furthermore, the carbon dioxide hydrogenation catalyst can be a supported manganese oxide catalyst including one or more auxiliary metals selected from the group consisting of La, Ca, K, W, Cu and Al. The carbon dioxide hydrogenation catalyst can also be a metal oxide catalyst including molybdenum and nickel.

The carbon dioxide hydrogenation process can be carried out in a temperature of from about 300° C. to about 900° C., at a pressure of from about 0.1 mPa to about 5 MPa, and with a contact time of about 0.5 s to about 6 s. In some embodiments, the gaseous feed mixture includes hydrogen and carbon dioxide in a ratio of from about 1 to about 5.

A first syngas mixture can be produced from the methane steam reforming process. The first syngas mixture produced from the methane steam reforming process has a temperature of from about 450° C. to about 900° C. In one embodiment, the first syngas mixture has a temperature of about 850° C. A second syngas mixture can be produced from the carbon dioxide hydrogenation process. In certain embodiments, the processes of the presently disclosed subject matter include mixing the first syngas mixture produced from the methane steam reforming process and the second syngas mixture produced from the carbon dioxide hydrogenation process. In other embodiments, the processes include mixing the first syngas mixture produced from the methane steam reforming process with the gaseous feed mixture prior to the carbon dioxide hydrogenation process. The first syngas mixture produced from the methane steam reforming process can heat the gaseous feed mixture to about 750° C. The first syngas mixture produced from the methane steam reforming process and the heated the gaseous feed mixture are subsequently subject to the carbon dioxide hydrogenation process.

The term "about" or "substantially" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

The presently discloses subject matter provides processes and apparatuses for synthesizing methanol. The processes include obtaining a syngas mixture from an integrated carbon dioxide hydrogenation process and a methane steam reforming process. The carbon dioxide hydrogenation process includes contacting a gaseous feed mixture that includes carbon dioxide and hydrogen with a carbon dioxide hydrogenation catalyst. The methane steam reforming process includes contacting a desulphurised gaseous hydrocarbon feedstock and steam with a methane reforming catalyst. The processes include contacting the syngas mixture with a methanol catalyst to obtain a product stream including methanol. The processes can further include removing water from the syngas mixture prior to contacting the syngas mixture with the methanol catalyst.

Methane Steam Reforming Processes

The methane steam reforming process of the presently disclosed subject matter can be performed in conventional reactors and apparatuses, e.g., the conventional widely used top-fired or side-fired reformers. The reactor can include a nickel-based methane reforming catalyst, usually in the form of small cylinders or rings. The syngas mixture obtained from the methane steam reforming can have a SN of about 2.0 to about 3.5, e.g., about 2.0 to about 2.5, about 2.5 to about 3.0, or about 3.0 to about 3.5. In one embodiment, the SN of the syngas mixture obtained from the methane steam reforming process is about 2.9. In another embodiment, the SN of the syngas mixture obtained from the methane steam reforming process is about 3.2. For methanol synthesis, a syngas composition having a SN of about 2.0 is preferred. The SN value of the syngas composition can be lowered by methods and processes known to one of ordinary skill in the art, e.g., by adding $CO_2$.

In the methane reforming process of the presently disclosed subject matter, the gaseous hydrocarbon feedstock can be any hydrocarbon mixture having a H/C ratio of about 2 to about 4 that is gaseous at reactor inlet operating conditions, i.e., at about 300° C. Suitable examples include hydrocarbons like methane, ethane, methane-rich mixtures, or light naphtha (mixture of mainly C5-C9 paraffin compounds).

One suitable example of a methane-rich feedstock is natural gas obtained from gas or oil fields. The primary component of natural gas is methane, which is generally present in an amount of from about 80 mol % to about 97 mol %. Natural gas can also include other gaseous hydrocarbons, e.g., ethane, typically from about 3 mol % to about 15 mol % of propane and butane and small amounts of higher hydrocarbons (generally less than about 5 mol % in total), as well as sulphur-containing gases, like hydrogen sulphide, in varying amounts. Further minor (or even trace) amounts of nitrogen, helium, carbon dioxide, water, odorants, and metals like mercury can also be present.

Organo-sulphur compounds and hydrogen sulphide are common contaminants of hydrocarbons from natural sources, which should be removed prior to use of hydrocarbon gas as a feedstock in the methane steam reforming process, to avoid poisoning of reforming catalysts. Desulphurisation can be done with conventional techniques. In certain embodiments, the hydrocarbon gaseous feedstock is first compressed to about 3 milliPascals (mPa) to about 4 MegaPascals (MPa) with a centrifugal or reciprocating compressor. A hydrogen-rich stream (e.g., a purge stream from a methanol synthesis loop) is mixed with the gas, usually after compression, and hydrogen concentration in the gas is maintained at a level of about 2 volume percent (vol %) to about 5 vol %. The stream can be pre-heated to about 350° C. to about 380° C. and can be passed over an adiabatic catalytic reactor containing a hydrodesulphurisation catalyst, e.g., Co—Mo— or Ni—Mo-based. The organo-sulphur compounds in the feedstock are converted to $H_2S$, which is subsequently removed by passing over a suitable absorbent, like ZnO, in a downstream vessel. The sulphur content of the desulphurised hydrocarbon gaseous feed of the presently disclosed subject matter can be at a level of less than 1 part per million (ppm). In certain embodiments, the desulphurised hydrocarbon feedstock used in the methane steam reforming process is a methane-rich feedstock, which includes at least about 75 mole percent (mol %) of methane (based on the total hydrocarbon content of the feedstock), e.g., at least about 80 mol %, at least about 85 mol %, at least about 90 mol %, at least about 92 mol %, at least about 94 mol %, or at least about 96 mol % of methane.

In accordance with the methane reforming process of the presently disclosed subject matter, the desulphurised hydrocarbon feedstock can be mixed with steam and then fed to a gas heated reformer (GHR) and a steam methane reformer (SMR) that operated in series. Mixing the desulphurised hydrocarbon feedstock with steam can be done at a pressure of from about 3 to about 5 MPa and a temperature of about 350° C. to about 400° C. The desulphurised hydrocarbon feedstock mixed with steam can have a steam to carbon ratio of about 2.0 to about 3.5, e.g., about 2.2 to about 3.0, or from about 2.3 to about 2.7. In some embodiments, the desulphurised hydrocarbon feedstock mixed with steam can be preheated to about 500° C. to about 550° C., e.g., a heat exchanger. A heat exchanger coil can be installed in the convection duct of the steam methane reformer of the methane steam reforming unit.

The preheated desulphurised hydrocarbon feedstock mixed with steam can be subsequently fed to a conventional gas heated reformer (GHR). The gas heated reformer can include a methane reforming catalyst, which can be a Ni-based reforming catalyst. In the GHR, higher hydrocarbons, if any, can be converted, and part of the methane can be steam reformed to CO, $CO_2$ and $H_2$. The extent of reforming can depend on various factors, including, but not limited to feed pre-heat temperature, operating pressure, feed gas composition and steam to carbon ratio. Any GHR designs known to one of ordinary skill in the art can be applied to make a unit of suitable size for the methane reforming process of the presently disclosed subject matter. The operating conditions of the GHR can include a pressure of from about 2 MPa to about 4 MPa and a temperature of about 500° C. to about 870° C. (e.g., about 600° C. to about 700° C.).

The partly reformed gas stream coming from the GHR can have a temperature of about 600° C. to about 700° C. (e.g., about 625° C. to about 675° C.), and can be subsequently fed to the steam methane reactor (SMR) unit at a pressure of about 2 MPa to about 4 MPa. Any SMR designs known to one of ordinary skill in the art can be applied to make a unit of suitable size for the presently disclosed methane steam reforming process. The operating conditions for SMR can include a pressure of about 1 MPa to about 4 MPa (e.g., about 3 MPa to about 4 MPa), and a temperature of about 450° C. to about 900° C. (e.g., about 700° C. to about 900° C., or about 800° C. to about 880° C.).

CO2 Hydrogenation Processes

The $CO_2$ hydrogenation processes of the presently disclosed subject matter can be performed in conventional reactors and apparatuses, including, but not limited to, those used in $CH_4$ reforming. One of ordinary skill in the art will be able to select a suitable reactor set-up depending on specific conditions and circumstances. Suitable types of reactors include, but are not limited to, continuous fixed bed reactors. Given the high reaction temperature, and the catalytic activity of certain metals, e.g., Ni in methanation reactions, use of a material including Ni or other active metals for making reactor walls should generally be avoided. For this reason, the reactors used in connection with the processes of the presently disclosed subject matter are generally lined with inert materials, e.g., glass linings for relevant reactor parts of the reactors.

In accordance with the presently disclosed subject matter, $CO_2$ is selectively converted into CO by a reverse water gas shift (RWGS) reaction in the presence of a $CO_2$ hydrogenation catalyst. The resulting product of this $CO_2$ hydrogenation process is a gas mixture containing CO and water, and non-converted $CO_2$ and $H_2$, which can be represented by the following equation:

$$CO_2 + nH_2 \leftrightarrows CO + (n-1)H_2 + H_2O$$

In the above equation, n may vary widely, e.g., from n=1 to n=5, to result in a syngas composition, e.g., expressed as its $H_2$/CO ratio or as SN, which can consequently vary within wide limits.

The water formed in this $CO_2$ hydrogenation process can be removed from the product stream driving the equilibrium of the reaction in the desired direction, because water often interferes with subsequent reactions utilizing the syngas. Water can be removed from the product stream with any suitable method known in the art, e.g., condensation, liquid/gas separation, etc.

In accordance with the presently disclosed subject matter, the $CO_2$ hydrogenation processes include contacting a gaseous feed mixture including $CO_2$ and $H_2$ with a $CO_2$ hydrogenation. The $CO_2$ hydrogenation processes can be performed over a wide temperature range. As the reaction is endothermic, a high temperature will promote conversion, but too high temperature may also induce unwanted reactions. The $CO_2$ hydrogenation process can be performed under isothermal conditions at a temperature of about 300° C. to about 900° C., e.g., about 300° C. to about 400° C., about 400° C. to about 500° C., about 500° C. to about 600° C., about 530° C. to about 600° C., about 540° C. to about 580° C., about 560° C. to about 570° C., about 600° C. to about 700° C., or about 700° C. to about 800° C.

The $CO_2$ hydrogenation processes can be performed over a wide pressure range. A higher pressure tends to enable lower reaction temperatures, but very high pressures are not practical. Thus, the operating pressure can be about 0.1 MPa to about 6 MPa, e.g., about 1.5 MPa to about 5 MPa, or about 2 MPa to about 4 MPa.

The contact time of contacting the gaseous feed mixture containing $CO_2$ and $H_2$ with a $CO_2$ hydrogenation catalyst according to the $CO_2$ hydrogenation processes of the presently disclosed subject matter can vary widely, but is generally from about 0.5 seconds (s) to about 6 s, e.g., from about 1.5 s to about 5 s, or from about 2 s to about 4 s.

In certain embodiments, the SN of the syngas mixture produced from the $CO_2$ hydrogenation processes of the presently disclosed subject matter is about 0.1 to about 3.5, e.g., about 0.1 to about 1.0, about 1.0 to about 2.0, about 2.0 to about 2.5, about 2.5 to about 3.0, or about 3.0 to about 3.5. In one embodiment, the SN of the syngas mixture produced from the $CO_2$ hydrogenation processes is about 3.2. In some embodiments, the SN of the syngas mixture produced from the $CO_2$ hydrogenation processes is about 1.5 to about 2.0, e.g., about 1.7 or about 1.9. In some embodiments, the SN of the syngas mixture produced from the $CO_2$ hydrogenation processes is about 2.0 to about 2.5, e.g., about 2.0, about 2.1, about 2.2, about 2.3, about 2.4, or about 2.5. The SN of the syngas mixture produced from the $CO_2$ hydrogenation processes of the presently disclosed subject matter can be adjusted to the suitable SN for methanol synthesis, e.g., about 2.0.

In one embodiment, the gaseous feed mixture for the $CO_2$ hydrogenation processes includes equal-molar amounts of $CO_2$ and $H_2$. In another embodiment, the gaseous feed mixture includes $CO_2$ and $H_2$ in a molar ratio of 1:2, resulting in a syngas composition with a SN of about 1.0. In yet another embodiment, the gaseous feed mixture includes $CO_2$ and $H_2$ in a molar ratio of 1:3, resulting in a syngas composition with a SN of about 2.0; which can be advantageously used for methanol synthesis.

The $H_2$ in the gaseous feed mixture used in the $CO_2$ hydrogenation processes of the presently disclosed subject matter can originate from various sources, including streams coming from other chemical process, e.g., ethane cracking, methanol synthesis, or conversion of $CH_4$ to aromatics.

The $CO_2$ in the gaseous feed mixture used in the $CO_2$ hydrogenation processes of the presently disclosed subject matter can originate from various sources. In certain embodiments, the $CO_2$ comes from a waste gas stream, e.g., from a plant on the same site, e.g., from ammonia synthesis, optionally with (non-catalytic) adjustment of the gas composition, or after recovering $CO_2$ from a gas stream. Recycling such $CO_2$ as starting material in the processes of the presently disclosed subject matter thus contributes to reducing the amount of $CO_2$ emitted to the atmosphere (from a chemical production site). The $CO_2$ used as feed may also at least partly have been removed from the effluent gas of the process itself and recycled back to the reactor in the feed mixture.

The $CO_2$ hydrogenation catalyst used in the $CO_2$ hydrogenation processes of the presently disclosed subject matter can include Mn oxide, and an oxide of a redox metal having certain basic properties, e.g., at least one member selected from the group consisting of Cr, Ni, La, Ce, W, and Pt. Elements of more acidic nature can promote undesirable side-reactions, especially coke methane formation. In addition, presence of these redox metals can lead to better dispersion of the metal components and reduces the risk of agglomeration of active sites. In some embodiments, the $CO_2$ hydrogenation catalyst includes oxides of Mn and Ce and/or La. In one embodiment, the $CO_2$ hydrogenation catalyst includes Mn and La, which exhibit high CO₂ conversion. Details of CO$_2$ hydrogenation catalysts used in CO$_2$ hydrogenation processes including Mn are described in U.S. Patent Application Publication No. 2010/0190874, which is hereby incorporated by reference in its entirety.

Additionally, the CO$_2$ hydrogenation catalysts of the presently disclosed subject matter can include chromium as active constituent. The CO$_2$ hydrogenation catalyst can include alumina as its support material, and can further include an alkali or alkaline earth metal as promoter. The CO$_2$ hydrogenation catalyst can also include other inert components, like a binder material, or usual impurities, as known to one of ordinary skill in the art. Details of CO$_2$ hydrogenation catalysts including chromium as an active constituent used in CO$_2$ hydrogenation processes are disclosed in U.S. Pat. No. 8,288,446, which is hereby incorporated by reference in its entirety.

Furthermore, the CO$_2$ hydrogenation catalysts of the presently disclosed subject matter can be a supported manganese oxide catalyst including at least one auxiliary metal selected from the group consisting of La, Ca, K, W, Cu, and Al. Details of supported manganese oxide catalysts used in CO$_2$ hydrogenation processes are disclosed in U.S. Patent Application Publication No. 2013/0150466, which is hereby incorporated by reference in its entirety.

In other embodiments, the CO$_2$ hydrogenation catalysts of the presently disclosed subject matter can include Ni and a support material. In one embodiment, the support material is lanthana (La$_2$O$_3$). Details of CO$_2$ hydrogenation Ni/La$_2$O$_3$ catalysts used in CO$_2$ hydrogenation processes are described in U.S. Patent Application Publication No. 2012/0007025, which is hereby incorporated by reference in its entirety.

In addition, the CO$_2$ hydrogenation catalyst of the presently disclosed subject matter can be a metal oxide catalyst including molybdenum and nickel. In some embodiments, methane can be added to the gaseous feed mixture to produce syngas mixture. Details of metal oxide catalysts used in CO$_2$ hydrogenation processes are disclosed in International Patent Application No. PCT/US2015/010282, filed on Jan. 6, 2015, which is hereby incorporated by reference in its entirety.

The CO$_2$ hydrogenation catalysts used in the CO$_2$ hydrogenation processes according to the presently disclosed subject matter can further include an inert carrier or support material or combination of carriers or support materials, of a certain particle size and geometry. In certain embodiments, the geometric form of the catalyst comprises spherical pellets, extrudates, tablets, rings, or other convenient forms.

Suitable supports can be any support materials exhibiting good stability at the reaction conditions to be applied in the process of the presently disclosed subject matter, and are known by one of ordinary skill in the art of catalysis or mixtures of support materials. In certain embodiments, the support material is at least one member selected from the group consisting of alumina, magnesia, silica, titania, zirconia and mixtures or combinations thereof.

The catalysts used in the processes of the presently disclosed subject matter can be prepared by any conventional catalyst synthesis method as known in the art. Generally such process includes making aqueous solutions of the desired metal components, for example, from their nitrate or other soluble salt; mixing the solutions optionally with a support material; forming a solid catalyst precursor by precipitation (or impregnation) followed by removing water and drying; and then calcining the precursor composition by a thermal treatment in the presence of oxygen.

Integrated Synthesis Processes

Figure 1:
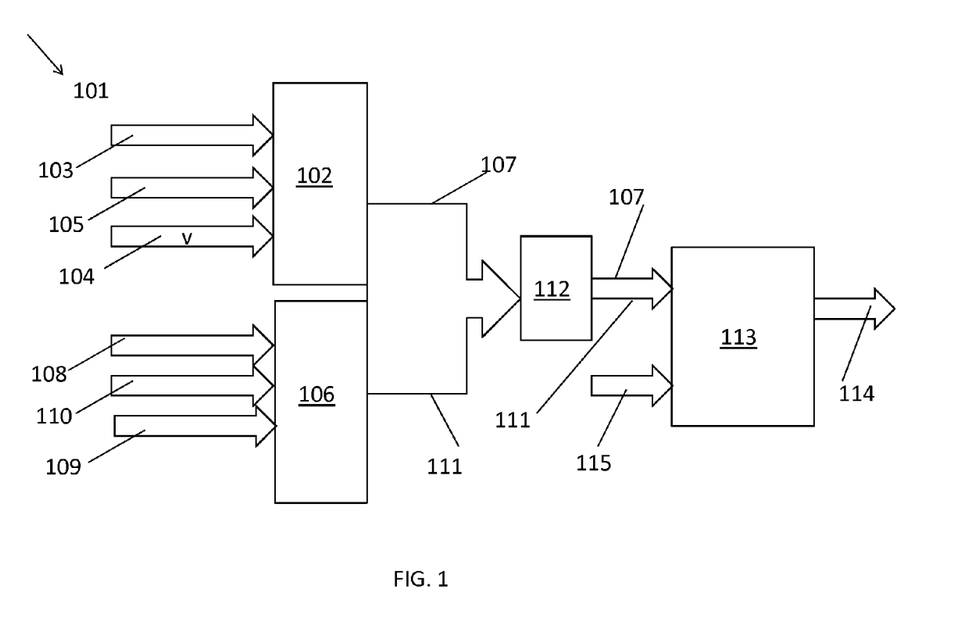
FIG. 1 shows a process for synthesizing methanol in accordance with one non-limiting exemplary embodiment of the presently disclosed subject matter.

The processes of the presently disclosed subject matter integrates or combines a CO$_2$ hydrogenation process and a methane steam reforming process. Since CO$_2$ hydrogenation process and a methane steam reforming process both produce a syngas mixture including CO, H$_2$, and CO$_2$, these two processes can be integrated to provide syngas mixture to synthesize methanol. A methane steam reforming process is more energy consuming than a CO$_2$, hydrogenation process, e.g., enthalpy of a methane steam reforming process is about five times more than that of a CO$_2$ hydrogenation process, for example, the ΔH of a methane steam reforming process is about 206 kiloJoules per mole (kJ/mol), while the ΔH of a CO$_2$ hydrogenation process is about 41 kJ/mol. The integrated processes of the presently disclosed subject matter can reduce energy consumption of the methane steam reforming process, thereby reducing the syngas production cost. The integration of these two processes is an energetic integration. The integrated process of the presently disclosed subject matter can include performing a CO$_2$ hydrogenation process and a methane steam reforming process independently and/or in parallel, obtaining the syngas mixtures produced from both processes, respectively, and contacting the syngas mixture with a methanol catalyst to obtain a product stream comprising methanol. For the purpose of illustration and not limitation, FIG. 1 (also referred to herein as "FIG.") shows an integrated process for synthesizing methanol in accordance with one embodiment of the disclosed subject matter. As shown in FIG. 1, the presently disclosed integrated process 101 includes a CO$_2$ hydrogenation process 102 and a methane steam reforming process 106. In the CO$_2$ hydrogenation process 102, CO$_2$ 103 can react with H$_2$ 104 with the aid of a CO$_2$ hydrogenation catalyst 105 to produce a syngas mixture 107. In the methane steam reforming process 106, CH$_4$ 108 can be reformed by steam 109 with the aid of a methane steam reforming catalyst 110 to obtain a syngas mixture 111. The syngas mixture 107 obtained from the CO$_2$ hydrogenation process and the syngas mixture 111 obtained from the methane steam reforming process have the same composition, e.g., CO, H$_2$, CO$_2$, sometimes CH$_4$, H$_2$O and N$_2$. The integrated process 101 can include a water separation process 112, where water is separated from the syngas mixtures 107 and 111 obtained from the CO$_2$ hydrogenation process 102 and from the methane steam reforming process 106. The integrated process 101 further includes a methanol synthesis process 113, where methanol 114 is produced from the syngas mixtures 107 and 111 with the aid of a methanol catalyst 115.

The reformed syngas mixture produced from a methane steam reforming process can have a temperature of about 450° C. to about 900° C., e.g., about 700° C. to about 900° C., or 800° C. to about 880° C. In one embodiment, the temperature of the reformed syngas mixture produced from the methane steam reforming process is about 850° C. The reformed syngas mixture produced from the methane steam reforming process can heat the mixture of CO$_2$ and H$_2$ to a temperature suitable for a CO$_2$ hydrogenation process, e.g., about 750° C. The syngas mixture produced from the CO$_2$ hydrogenation process can have a temperature of about 500° C. to about 600° C., e.g., about 560° C. Thus, the CO$_2$ hydrogenation process can cool down the reformed syngas mixture from the methane steam reforming process, e.g., to about 560° C.

A CO$_2$ hydrogenation process can include heating the gaseous feed mixture by the heat of the reformed syngas mixture obtained from a mental steam reforming process.

Figure 2:
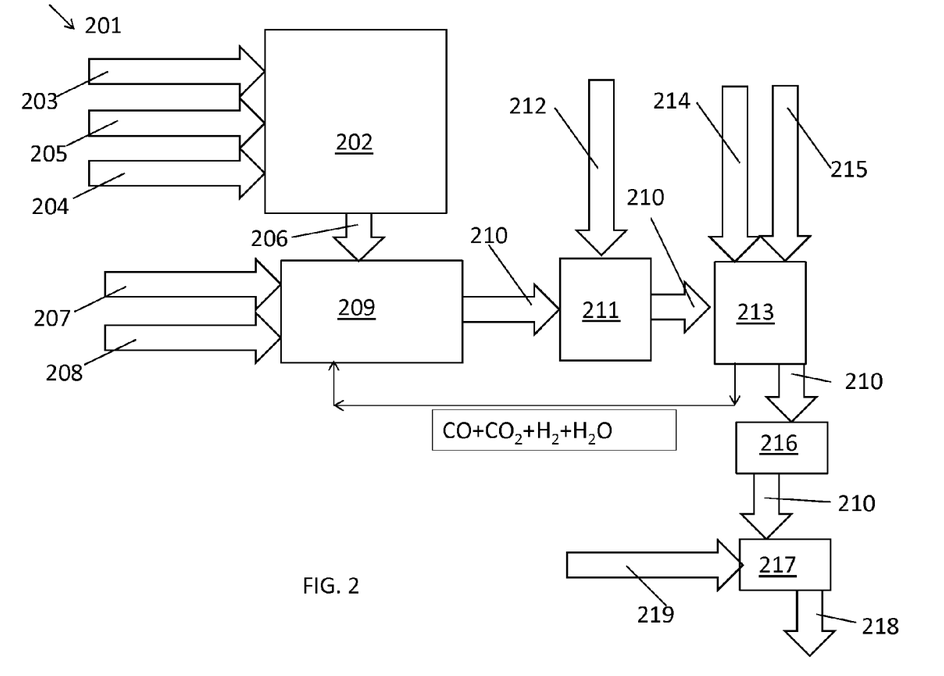
FIG. 2 shows a process for synthesizing methanol in accordance with one non-limiting exemplary embodiment of the presently disclosed subject matter.

Alternatively or additionally, the integrated process of the presently disclosed subject matter can include integrating the syngas mixture with the gaseous feed mixture including $CO_2$ and $H_2$ for a $CO_2$ hydrogenation process. The heat of the reformed syngas mixture obtained from the methane steam reforming process can be utilized to heat $CO_2$ and $H_2$. For the purpose of illustration and not limitation, FIG. 2 shows an integrated process for synthesizing methanol in accordance with one embodiment of the disclosed subject matter. As shown in FIG. 2, the presently disclosed integrated process 201 includes a methane steam reforming process 202. In the methane steam reforming process 202, $CH_4$ 203 can be reformed by steam 204 with the aid of a methane steam reforming catalyst 205 to obtain a syngas mixture 206. The reformed syngas mixture 206 coming from the methane steam reforming process 202 can have a temperature of about 450° C. to about 900° C., e.g., about 700° C. to about 900° C., or 800° C. to about 880° C. In one embodiment, the temperature of the reformed syngas mixture from the methane steam reforming process is about 850° C. The reformed syngas mixture from the methane steam reforming process 206 can be mixed with a gaseous feed mixture including $CO_2$ 207 and $H_2$ 208 in a first heat exchange process 209 to $CO_2$ and $H_2$. $CO_2$ and $H_2$ can be heated by the reformed syngas mixture from the methane steam reforming process to a temperature suitable for a $CO_2$ hydrogenation process, e.g., about 750° C. The syngas mixture 210 that includes CO, $CO_2$, $H_2$ and $H_2O$ proceeds to a $CO_2$ hydrogenation process 211. In the $CO_2$ hydrogenation process 211, $CO_2$ can react with $H_2$ to produce CO, $H_2$ and $H_2O$ with the aid of a $CO_2$ hydrogenation catalyst 212 according to the following equation:

$$CO_2 + nH_2 \leftrightarrow CO + (n-1)H_2 + H_2$$

The syngas mixture 210 that includes CO, $CO_2$, $H_2$ and $H_2O$ coming from the $CO_2$ hydrogenation process 211 can have a temperature of about 500° C. to about 600° C., e.g., about 560° C. The presently disclosed integrated process 201 can also include a second heat exchange process 213 that receives $CO_2$ 214 and $H_2$ 215 and the syngas mixture 210 coming from the $CO_2$ hydrogenation process 211 and utilizes the heat of the syngas mixture 210 to pre-heat $CO_2$ 214 and $H_2$ 215. The pre-heated $CO_2$ and $H_2$ from the second heat exchange process are fed to the first heat exchange 209. The presently disclosed integrated process 201 can further include a water separation process 216, where water is separated from the syngas mixtures 210. The integrated process 201 further includes a methanol synthesis process 217, where methanol 218 is produced from the syngas mixtures 210 with the aid of a methanol catalyst 219.

The following example are merely illustrative of the device disclosed herein and are not intended to limit the scope hereof.

EXAMPLES

The following examples are merely illustrative of the presently disclosed subject matter and they should not be considered as limiting the scope of the presently disclosed subject matter in any way.

Example 1

A glass tube filled with $Mn/La_2O_3$ catalyst was applied to a $CO_2$ hydrogenation reactor. A gaseous feed mixture was made by mixing $CO_2$ and $H_2$, and was passed through the reactor tube with an inlet flow rate of about 52.5 milliliters per minute (ml/min) and an outlet flow rate of about 47 ml/min. The gaseous feed mixture included about 23 mol % $CO_2$ and about 77 mol % $H_2$. The gaseous feed mixture was contacted with the $Mn/La_2O_3$ catalyst at about 580° C. for between about 2 seconds and about 7 seconds to produce a syngas mixture. The reaction was performed at the atmospheric pressure. The composition of the resulting syngas mixture product was measured by gas chromatography, after removing water from the mixture in a cold trap. Table 1 shows the resulting syngas mixture composition.

TABLE 1

| Syngas Gas Composition (mol %) | | | | | |
|---|---|---|---|---|---|
| $H_2$ | $CO_2$ | CO | $N_2$ | $O_2$ | SN |
| 74.5 | 12.8 | 12.7 | — | — | 2.42 |

Example 2

A gaseous feed mixture was made by mixing $CO_2$ and $H_2$, and was passed through the reactor tube with an inlet flow rate of about 52 ml/min and an outlet flow rate of about 47 ml/min. The gaseous feed mixture included about 23 volume % $CO_2$ and about 76.5 volume % $H_2$. The gaseous feed mixture was contacted with a $LiMnO_2$-$Cr/Al_2O_3$ catalyst at about 680° C. to produce a syngas mixture. Table 2 shows the resulting syngas mixture composition measured after a 15-day reaction.

TABLE 2

| Syngas Gas Composition (volume %) | | | |
|---|---|---|---|
| CO | $H_2$ | $CO_2$ | SN |
| 10.3 | 75.3 | 14.2 | 2.49 |

Example 3

A gaseous feed mixture was made by mixing $CO_2$ and $H_2$, and was passed through the reactor tube with an inlet flow rate of about 52 ml/min. The gaseous feed mixture included about 25 volume % $CO_2$ and about 75 volume % $H_2$. The gaseous feed mixture was contacted with a 40 mesh particle size of $Cr/Al_2O_3$ catalyst at about 600° C. to produce a syngas mixture. Table 3 shows the resulting syngas mixture composition measured after a 1-month reaction, a 2-month reaction, a 3-month reaction, a 4-month reaction, and a 5-month reaction.

TABLE 3

| Duration | Syngas Gas Composition (mol %) | | |
|---|---|---|---|
| (months) | $CO_2$ | $H_2$ | CO |
| 1 | 11.76 | 69.7 | 17.9 |
| 2 | 11.07 | 72.3 | 16.6 |
| 3 | 12.01 | 71.9 | 16.0 |
| 4 | 11.37 | 72.0 | 16.6 |
| 5 | 11.01 | 73.0 | 15.9 |

Example 4

A gaseous feed mixture was made by mixing $CO_2$ and $H_2$, and was passed through the reactor tube with an inlet flow rate of about 50 ml/min. The gaseous feed mixture included about 25 volume % $CO_2$ and about 75 volume % $H_2$. The gaseous feed mixture was contacted with about 3 ml of a Mo—Ni catalyst at about 560° C. to produce a syngas mixture. Table 4 shows the resulting syngas mixture composition measured after a 1-month reaction, a 2-month reaction, and a 3-month reaction.

TABLE 4

| Duration | Syngas Gas Composition (mol %) | | | |
|---|---|---|---|---|
| (months) | CO | $CO_2$ | $H_2$ | $CH_4$ |
| 1 | 16.8 | 12.4 | 68.5 | 1.98 |
| 2 | 17.5 | 13.6 | 66.8 | 1.96 |
| 3 | 17.4 | 13.5 | 65.6 | 3.44 |

Example 5

A comparison of the syngas mixture produced by a $CO_2$ hydrogenation process and a methane steam reforming process was performed. The results are shown in Table 4.

TABLE 5

| methane steam reforming | | | | | | $CO_2$ hydrogenation | | | | |
|---|---|---|---|---|---|---|---|---|---|---|
| Syngas composition (mol %) | | | | | | Syngas composition (mol %) | | | | |
| $H_2$ | CO | $CO_2$ | $CH_4$ | $N_2$ | SN | $H_2$ | CO | $CO_2$ | SN | Catalyst |
| 74.1 | 14.7 | 7.89 | 3.2 | 0.2 | 2.9 | 74.2 | 12.9 | 12.8 | 2.4 | Cr/$Al_2O_3$ |

The process disclosed herein include at least the following embodiments:

Embodiment 1: A process of synthesizing methanol, comprising: obtaining a syngas mixture from an integrated carbon dioxide hydrogenation process and a methane steam reforming process, wherein the carbon dioxide hydrogenation process comprises contacting a gaseous feed mixture comprising carbon dioxide and hydrogen with a carbon dioxide hydrogenation catalyst; and the methane steam reforming process comprises contacting a desulphurised gaseous hydrocarbon feedstock and steam with a methane reforming catalyst; and contacting the syngas mixture with a methanol catalyst to obtain a product stream comprising methanol.

Embodiment 2: The process of Embodiment 1, further comprising removing water from the syngas mixture prior to contacting the syngas mixture with the methanol catalyst.

Embodiment 3: The process of Embodiment 1 or Embodiment 2, wherein the desulphurised gaseous hydrocarbon feedstock is a methane-rich feedstock comprising at least about 75 mol % of methane.

Embodiment 4: The process of any of Embodiments 1-3, wherein the desulphurised gaseous hydrocarbon feedstock is mixed with the steam at a steam/carbon ratio of from about 2.0 to about 3.5.

Embodiment 5: The process of any of Embodiments 1-4, wherein the desulphurised gaseous hydrocarbon feedstock mixed with the steam is fed to a gas heated reformer and a steam methane reformer operated in series.

Embodiment 6: The process of any of Embodiments 1-5, wherein the desulphurised gaseous hydrocarbon feedstock mixed with the steam is pre-heated to from about 500° C. to about 550° C. and then fed to the gas heated reformer.

Embodiment 7: The process of any of Embodiments 1-6, wherein the reformed gas coming from the gas heated reformer has a temperature of from about 600° C. to about 700° C., and is subsequently fed to the steam methane reformer.

Embodiment 8: The process of any of Embodiments 1-7, wherein the syngas mixture comprises carbon monoxide, carbon dioxide, and hydrogen.

Embodiment 9: The process of any of Embodiments 1-8, wherein the syngas mixture has a stoichiometric number of about 2.0.

Embodiment 10: The process of any of Embodiments 1-9, wherein the methane reforming catalyst comprises nickel.

Embodiment 11: The process of any of Embodiments 1-10, wherein the carbon dioxide hydrogenation catalyst is selected from: a catalyst comprising manganese oxide, and an oxide of at least one member selected from the group consisting of calcium, potassium, copper, aluminum, chromium, nickel, lanthanum, cerium, tungsten and platinum; a catalyst comprising nickel; a catalyst comprising chromium; a catalyst comprising molybdenum and nickel; or a combination comprising at least one of the foregoing.

Embodiment 12: The process of Embodiment 11, wherein the carbon dioxide hydrogenation catalyst further comprises a support material selected from the group consisting of lanthana oxide and aluminum oxide.

Embodiment 13: The process of Embodiment 11, wherein the catalyst comprising chromium further comprises a promoter comprising one alkali metal or alkaline earth metal.

Embodiment 14: The process of any of Embodiments 1-13, wherein the carbon dioxide hydrogenation process is carried out in a temperature of about 300° C. to about 900° C., at a pressure of about 0.1 mPa to about 5 MPa, and with a contact time of about 0.5s to about 6s.

Embodiment 15: The process of any of Embodiments 1-14, wherein the gaseous feed mixture comprises hydrogen and carbon dioxide in a ratio of from about 1 to about 5.

Embodiment 16: The process of any of Embodiments 1-15, wherein a first syngas mixture is produced from the methane steam reforming process.

Embodiment 17: The process of any of Embodiments 1-16, wherein the first syngas mixture produced from the methane steam reforming process has a temperature of from about 450° C. to about 900° C.

Embodiment 18: The process of Embodiment 17, wherein the first syngas mixture produced from the methane steam reforming process has a temperature of about 850° C.

Embodiment 19: The process of Embodiment 16, wherein a second syngas mixture is produced from the carbon dioxide hydrogenation process.

Embodiment 20: The process of Embodiment 19, comprising mixing the first syngas mixture produced from the methane steam reforming process and the second syngas mixture produced from the carbon dioxide hydrogenation process.

Embodiment 21: The process of Embodiment 16, comprising mixing the first syngas mixture produced from the methane steam reforming process with the gaseous feed mixture prior to the carbon dioxide hydrogenation process.

Embodiment 22: The process of Embodiment 21, wherein the first syngas mixture produced from the methane steam reforming process heats the gaseous feed mixture to about 750° C.

Embodiment 23: The process of Embodiment 22, wherein the first syngas mixture produced from the methane steam reforming process and the heated the gaseous feed mixture are subject to the carbon dioxide hydrogenation process.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "+10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference Although the presently disclosed subject matter and its advantages have been described in detail, it should be understood that various changes, substitutions and alterations can be made herein without departing from the spirit and scope of the presently disclosed subject matter as defined by the appended claims. Moreover, the scope of the presently disclosed subject matter is not intended to be limited to the particular embodiments described in the specification. Accordingly, the appended claims are intended to include within their scope such modifications.

The invention claimed is:

1. A process of synthesizing methanol, comprising:
obtaining a syngas mixture from an integrated carbon dioxide hydrogenation process and a methane steam reforming process, wherein the carbon dioxide hydrogenation process comprises contacting a gaseous feed mixture comprising carbon dioxide and hydrogen with a carbon dioxide hydrogenation catalyst; and the methane steam reforming process comprises contacting a desulphurised gaseous hydrocarbon feedstock and steam with a methane reforming catalyst; and
contacting the syngas mixture with a methanol catalyst to obtain a product stream comprising methanol.

2. The process of claim 1, further comprising removing water from the syngas mixture prior to contacting the syngas mixture with the methanol catalyst.

3. The process of claim 1, wherein the desulphurised gaseous hydrocarbon feedstock is a methane-rich feedstock comprising at least about 75 mol % of methane.

4. The process of claim 1, wherein the desulphurised gaseous hydrocarbon feedstock is mixed with the steam at a steam/carbon ratio of from about 2.0 to about 3.5.

5. The process of claim 1, wherein the desulphurised gaseous hydrocarbon feedstock mixed with the steam is fed to a gas heated reformer and a steam methane reformer operated in series.

6. The process of claim 1, wherein the desulphurised gaseous hydrocarbon feedstock mixed with the steam is pre-heated to from about 500° C. to about 550° C. and then fed to the gas heated reformer.

7. The process of claim 1, wherein the syngas mixture comprises carbon monoxide, carbon dioxide, and hydrogen.

8. The process of claim 1, wherein the syngas mixture has a stoichiometric number of about 2.0.

9. The process of claim 1, wherein the methane reforming catalyst comprises nickel.

10. The process of claim 1, wherein the carbon dioxide hydrogenation process is carried out in a temperature of about 300° C. to about 900° C., at a pressure of about 0.1 mPa to about 5 MPa, and with a contact time of about 0.5 s to about 6 s.

11. The process of claim 1, wherein the gaseous feed mixture comprises hydrogen and carbon dioxide in a ratio of from about 1 to about 5.

12. The process of claim 1, wherein a first syngas mixture is produced from the methane steam reforming process, wherein the first syngas mixture produced from the methane steam reforming process has a temperature of from about 450° C. to about 900° C. s.

13. The process of claim 12, wherein the first syngas mixture produced from the methane steam reforming process has a temperature of about 850° C.

14. The process of claim 12, wherein a second syngas mixture is produced from the carbon dioxide hydrogenation process.

15. The process of claim 14, comprising mixing the first syngas mixture produced from the methane steam reforming process and the second syngas mixture produced from the carbon dioxide hydrogenation process.

16. The process of claim 12, comprising mixing the first syngas mixture produced from the methane steam reforming process with the gaseous feed mixture prior to the carbon dioxide hydrogenation process.

17. The process of claim 12, wherein the first syngas mixture produced from the methane steam reforming process and the heated the gaseous feed mixture are subject to the carbon dioxide hydrogenation process.

18. The process of claim 1, wherein the integrated process reduces energy consumption as compared to a methane steam reforming process.

19. The process of claim 1, wherein the gaseous feed mixture is contacted with the carbon dioxide hydrogenation catalyst at a temperature of about 300° C. to about 600° C.

20. The process of claim 1, wherein the carbon dioxide hydrogenation catalyst is selected from:
- a catalyst comprising manganese oxide, and an oxide of at least one member selected from the group consisting of calcium, potassium, copper, aluminum, chromium, nickel, lanthanum, cerium, tungsten and platinum;
- a catalyst comprising nickel;
- a catalyst comprising chromium;
- a catalyst comprising molybdenum and nickel; or
- a combination comprising at least one of the foregoing.

* * * * *